US009295762B2

(12) United States Patent
Everland et al.

(10) Patent No.: US 9,295,762 B2
(45) Date of Patent: *Mar. 29, 2016

(54) SCAFFOLDS FOR THE REGENERATION OF CARTILAGE (75) Inventors: Hanne Everland, Bagsvaerd (DK); Jacob Vange, Helsingoer (DK); Christian Clausen, Fredensborg (DK); Lene Feldskov Nielsen, Copenhagen K (DK)

(73) Assignee: Coloplast A/S, Humlebaek (DK)

( * ) Notice: Subject to any disclaimer, the term of this patent is extended or adjusted under 35 U.S.C. 154(b) by 558 days.

This patent is subject to a terminal disclaimer.

(21) Appl. No.: 12/450,012

(22) PCT Filed: Mar. 7, 2008

(86) PCT No.: PCT/EP2008/052781
§ 371 (c)(1),
(2), (4) Date: Sep. 8, 2009

(87) PCT Pub. No.: WO2008/107482
PCT Pub. Date: Sep. 12, 2008

(65) Prior Publication Data
US 2010/0034868 A1    Feb. 11, 2010

(30) Foreign Application Priority Data
Mar. 7, 2007  (DK) ................. 2007 00356

(51) Int. Cl.
*A61L 27/56* (2006.01)
*A61L 27/58* (2006.01)
*A61P 19/04* (2006.01)
(Continued)

(52) U.S. Cl.
CPC ................. *A61L 27/56* (2013.01); *A61L 27/48* (2013.01); *A61L 27/58* (2013.01); *A61L 2430/06* (2013.01)

(58) Field of Classification Search
None
See application file for complete search history.

(56) References Cited

U.S. PATENT DOCUMENTS

| 5,306,311 | A  | * | 4/1994  | Stone et al. ............... 623/14.12 |
| 2004/0197311 | A1 | * | 10/2004 | Brekke et al. ............... 424/93.7 |
| 2005/0187146 | A1 | * | 8/2005  | Helmus et al. .................... 514/8 |

FOREIGN PATENT DOCUMENTS

| WO | WO 94/09722 | | 5/1994 |
| WO | WO 2007/048831 A2 | | 5/2007 |
| WO | WO 2007048831 A2 | * | 5/2007 |

OTHER PUBLICATIONS

Avgoustakis, K. Pegylated Poly(Lactide) and Poly(Lactide-Co-Glycolide) Nanoparticles: Preparation, Properties, and Possible Applications in Drug Discovery. Current Drug Discovery. 2004, 1, 321-333.*

(Continued)

*Primary Examiner* — Isaac Shomer
*Assistant Examiner* — Michael P Cohen
(74) *Attorney, Agent, or Firm* — Coloplast Corp., Coloplast A/S; Nick Baumann (57) ABSTRACT The present application discloses that incorporation of dermatan sulfate and/or HA in composite scaffolds of certain polymers gives rise to a chondrogenic effect on chondrocytes resulting in formation of cartilage that resembles the natural ECM. This effect with dermatan sulfate as the primary additive has not previously been seen. The composites are formed by incorporation of dermatan sulfate finely dispersed particles optionally nanoparticles or as molecular dissolutions in a polymer matrix with no bonding between the DS and the matrix, providing the DS to the chondrocytes in an accessible non-crosslinked form.

11 Claims, 2 Drawing Sheets (51) Int. Cl.
*A61K 47/34* (2006.01)
*A61L 27/48* (2006.01)

(56) References Cited

OTHER PUBLICATIONS

Farndale, RW; Buttle, DJ; Barrett, AJ. Improved quantitation and discrimination of sulphated glycosaminoglycans by use of dimethylmethylene blue. Biochim. Biophys. Acta. 883 (1986) 173-179.*

Julia E. Babensee, Larry V. McIntire, and Antonios G. Mikos. Growth Factor Delivery for Tissue Engineering. Pharmaceutical Research, vol. 17, No. 5, 2000.*

Christopher G. Wilson, Lawrence J. Bonassar, and Sean S. Kohles. Modeling the dynamic composition of engineered cartilage. Archives of Biochemistry and Biophysics 408 (2002) 246-254.*

Arai, T., et al., "Heparin, Heparan Sulfate, and Dermatan Sulfate Regulate Formation of the Insulin-like Growth Factor-I and Insulin-like Growth Factor-binding Protein Complexes," Journal of Biological Chemistry, vol. 269, No. 32, pp. 20388-20393, Apr. 14, 1994.

Chevalier, X., et al., "Production of Binding Proteins and Role of the Insulin-like Growth Factor I Binding Protein 3 in Human Articular Cartilage Explants," British Journal of Rheumatology, vol. 35, No. 6, pp. 515-522, Jun. 1996.

Lee, C.T., "Biomimetic Porous Scaffolds Made from Poly(L-lactide)-g-chondroitin Sulfate Blend with Poly(L-lactide) for Cartilage Tissue Engineering," Biomacromolecules, vol. 7, No. 7, pp. 2200-2209, 2006.

Hodgkinson, S.C., et al., "Glycosaminoglycan Binding Characteristics of the Insulin-like Growth Factor-Binding Proteins," Journal of Molecular Endocrinology, vol. 13, pp. 105-112, 1994.

Fan, H., et al., Cartilage Regeneration using Mesenchymal Stem Cells and a PLGA-gelatin/chondroitin/hyaluronate Hybrid Scaffold, Biomaterials, vol. 27, pp. 4573-4580, 2006.

Yoo, H.S., et al., "Hyaluronic Acid Modified Biodegradable Scaffolds for Cartilage Tissue Engineering," Biomaterials, vol. 26, pp. 1925-1933, 2005.

Van Susante, J., et al., "Linkage of Chondroitin-Sulfate to Type I Collagen Scaffolds Stimulates the Bioactivity of Seeded Chondrocytes in Vitro," Biomaterials, vol. 22, pp. 2359-2369, 2001.

Møller, A.V., et al., "Glycosaminoglycans Increase Levels of Free and Bioactive IGF-I in Vitro," Journal of Endocrinology, vol. 155, pp. 297-305, 2006.

Penc, S.F., et al., "Dermatan Sulfate Released after Injury is a Potent Promoter of Fibroblast Growth Factor-2 Function," Journal of Biological Chemistry, vol. 273, No. 43, pp. 28116-28121, 1998.

Plaas, A., et al., "Chemical and Immunological Assay of the Nonreducing Terminal Residues of Chondroitin Sulfate from Human Aggrecan," Journal of Biological Chemistry, vol. 272, No. 33, pp. 20603-20610, 1997.

Smith, S. et al., "Heparan and Chondroitin Sulfate on Growth Plate Perlecan Mediate Binding and Delivery of FGF-2 to FGF Receptors," Matrix Biology, vol. 26, pp. 175-184, 2007.

Taylor, K.R., et al., "Structural and Sequence Motifs in Dermatan Sulfate for Promoting Fibroblast Growth Factor-2 (FGF-2) and FGF-7 Activity," Journal of Biological Chemistry, vol. 280, No. 7, pp. 5300-5306, 2005.

Trowbridge, J.M. et al., "Dermatan Sulfate: New Functions from an Old Glycosaminoglycan," Glycobiology, vol. 12, No. 9, pp. 117R-125R, 2002.

Chen, Y.L., et al., "Composite Chondroitin-6-sulfate/dermatan sulfate/chitosan Scaffolds for Cartilage Tissue Engineering," Biomaterials, vol. 28, pp. 2294-2305, 2007.

* cited by examiner

Fig. 4

SCAFFOLDS FOR THE REGENERATION OF CARTILAGE

This is a national stage of PCT/EP08/052781 filed Mar. 7, 2008 and published in English, which has a priority of Denmark no. PA 2007 00356 filed Mar. 7, 2007, hereby incorporated by reference.

FIELD OF THE INVENTION

The present invention relates to synthetic scaffolds for tissue repair and regeneration comprising a porous matrix consisting of a biodegradable polymer into which dermatan sulfate is incorporated.

BACKGROUND

Fibrin will be the normal scaffold for cells to invade in tissue repair. For several years, however, natural or synthetic polymers have been used for forming artificial scaffolds being applied to the damaged tissue for improving the repair process. Tissues are generally characterized in respect to functionality and appearance and are classified as hard or soft tissue. Soft tissue can further be categorized in cartilage and tendons opposed to loose connective tissue and muscles. The invention relates to both soft and hard tissue and the interface between these like in respect to cartilage and bone. Further the invention relates to synthetic scaffolds and to dermatan sulfate and derivatives of dermatan sulfate.

Cartilage is dense tissue composed of collagenous fibers and/or elastic fibers formed by the growth of chondrocytes all embedded in a firm gel-like matrix.

The matrix is mainly composed of proteoglycans filling the space between collagen fibers and is able to hold water. Continued synthesis, assembly and degradation by the chondrocytes maintain the structure and structural integrity of the extracellular matrix (ECM) of cartilage.

The proteoglycans are composed of a protein backbone and glycosamino glycans (GAG) linked to this. In the articular cartilage, the proteoglycans are of the aggrecan type containing mainly chondroitin- and keratan sulfate. Besides maintaining the physical and structural integrity of the cartilage, the GAGs are also involved in the cell adhesion, migration, proliferation and differentiation (Plaas A H K, Wong-Palms S, Roughley P J, Midure R J & Hascall V C. Chemical and immunological assay of the nonreducing terminal residues of chondroitin sulfate from human aggrecan. J. Biol. Chem. 272, 20603-20610 (1997)). Furthermore the GAGs form a network that protects the chondrocytes from the potentially damaging forces of mechanical function.

The function of the cartilage includes providing a framework upon which bone deposition can begin and supply a smooth surface for the movement of articulating bone. Cartilage is found in many different places in the body and can be found in three different types: hyaline, elastic and fibrocartilage. The different forms have special characteristics adapted to their function with the hyaline form being the most abundant type of cartilage. This form, named articular cartilage, is predominantly made of type II collagen and found lining bones in joints. This form of cartilage provides the joint with a low friction and wear-resistant bearing surface, that can tolerate a tremendous amount of repetitive physical stress.

Damaged articular cartilage has very little capacity for spontaneous healing, because of the hypocellularity and absence of both vascularization and innervation in the cartilage to support repair and remodeling.

Because of this lacking capacity for self-healing, many attempts have been made to facilitate the healing using scaffolds. As an attempt to mimic the ECM of cartilage, these are often made by incorporating various GAGs in a matrix of either natural or synthetic polymer. Important classes of GAGs are Hyaluronic acid (HA), Chondroitin Sulphate (CS), Heparan Sulfate (HS), Heparin, Keratan sulfate (KS) and Dermatan Sulphate (DS).

Yen-Lin Chen et al. (Composite chondroitin-6-sulfate/dermatan sulfate/chitosan scaffolds for cartilage tissue engineering. Biomaterials (2007)) describes the use of chitosan as the base material. A solution of this is freeze-dried to porous scaffolds, and varying amounts of CS and DS are bound covalently to this matrix. These scaffolds were seeded with chondrocytes. Overtly higher expression levels of aggrecan and collagen II was found in the CS+DS-containing scaffolds compared to the DS-only scaffolds. Cells in the DS-only scaffolds were clustered and no apparent lacuna was observed. DS-only was found to enhance GAG and collagen production, but did not stimulate cell proliferation.

Chic-Ta Lee, Ching-Ping Huang & Yu-Der Lee. (Biomimetic porous scaffolds made from poly(L-lactide)-g-chondroitin sulfate blend with poly(L-lactide) for cartilage tissue engineering. Biomacromolecules 7, 2200-2209 (2006)) describes how PLA is grafted to CS and a composite of this and PLA is made into porous scaffolds by solvent casting/particle leaching. These are seeded with mouse chondrocytes and cell adhesion, secretion of ECM, the quantity of synthesized collagen and GAGs and the compression modulus was then examined. The scaffold stimulated the growth of new cartilage, and after 4 weeks, the compression modulus was close to that of mouse cartilage.

Hyuk Sang Yoo, Eun Ah Lee, Jun Jin Yoon & Tae Gwan Park. (Hyaluronic acid modified biodegradable scaffolds for cartilage tissue engineering. Biomaterials 26, 1925-1933 (2005)) describes a blend of PLGA and PLGA-PEG-NH2 diblock copolymer made into porous scaffolds, and then HA is grafted to the surface. This is seeded with chondrocytes. It is concluded that the HA-immobilized scaffolds help the chondrocytes to retain their phenotype to a greater extent than the unmodified scaffold, and growth of new cartilage is observed within one month.

In Hongbin Fan et al. (Cartilage regeneration using mesenchymal stem cells and a PLGA-gelatin/chondroitin/hyaluronate hybrid scaffold. Biomaterials 26, 4573-4580 (2006)) a composite scaffold of PLGA and cross-linked gelatin/CS/HA is made and seeded with mesenchymal stem cells. The cells are induced to differentiate to chondrocytes, and seeded onto the scaffolds. In-vitro proliferation and GAG synthesis is examined. Scaffolds (both with and without gelatin/CS/HA) seeded with cells are implanted in rabbits with cartilage defects, and the rabbits are harvested after 6, 12 and 24 weeks. Both in-vitro and in-vivo results show superior results for the GAG-modified scaffold compared to plain PLGA. Both types gave formation of new cartilage in the rabbits, but the plain PLGA gave a thinner cartilage with inferior morphology.

Job L. C. van Susante et al. (Linkage of chondroitin-sulfate to type I collagen scaffolds stimulates the bioactivity of seeded chondrocytes in vitro. Biomaterials 22, 2359-2369 (2007)) describes how a solution of type I collagen is freeze dried to porous scaffolds. CS is then grafted to these and the scaffolds are seeded with chondrocytes. Cell proliferation and was higher in the CS-modified scaffold and growth of cartilage was better than in unmodified scaffolds.

In all the examples above, GAGs are grafted covalently to the base material. Because both CS and HA are abundant in the ECM of cartilage, these are often the first choice when making scaffolds.

SUMMARY

Hence prior art describes various ways to create scaffolds based on different types of materials and associated with GAGs for the support of tissue repair. Especially HA and CS have been considered favorable to use in scaffolds.

The present application discloses that incorporation of dermatan sulfate and/or HA in composite scaffolds of certain polymers gives rise to a chondrogenic effects on chondrocytes resulting in formation of cartilage that resemble the natural ECM. This effect with dermatan sulfate as the primary additive has not previously been seen. The composites are formed by incorporation of dermatan sulfate finely dispersed particles optionally nanoparticles or as molecular dissolutions in a polymer matrix with no bonding between the DS and the matrix, providing the DS to the chondrocytes in an accessible non-crosslinked form.

Thus, we have found a new and very simple way to stimulate the growth of new cartilage. By incorporating DS in a scaffold of the synthetic polymer and seeding this scaffold with human articular chondrocytes, we are able to stimulate the growth of new cartilage in 3 weeks. This new cartilage has excellent morphology and the presence of specific cartilage matrix proteins was demonstrated.

In comparison, cross-linked gelatin scaffolds with similar amounts of HA did not stimulate the growth of new cartilage—indeed the chondrocytes had no affinity for these scaffolds, and the scaffolds appeared acellular with no trace of cartilage 3 weeks after seeding with chondrocytes.

DETAILED DISCLOSURE

Throughout this disclosure, the following abbreviation will be used:

| | |
|---|---|
| 2-30 | MPEG-co-PLGA 2-30 kDa L:G 1:1 |
| CS | Chondroitin sulfate |
| DS | Dermatan sulfate |
| ECM | Extracellular matrix |
| EDC | 1-(3-Dimethylaminopropyl)-3-ethylcarbodiimide hydrochloride |
| FGF-2 | Fibroblast growth factor-2 |
| GAG | Glucosaminoglycan |
| HA | Hyaluronan |
| KS | Keratan sulfate |
| MPEG | methoxy-polyethylene glycol |
| PLGA | poly(lactide-co-glycolide) |

A central aspect of the present invention relates to a temporary scaffold comprising an accessible binder of FGF-2.

Various types of scaffolds exists.

In one aspect the temporary scaffold is synthetic. Such scaffolds are mainly degraded by hydrolysis in combination with enzymatic digestion. These scaffolds are preferably made from materials selected from the group consisting of PLA (polylactide), PGA (polyglycolide), PLGA (poly(lactide-co-glycolide)), MPEG-PLGA, PCL (polycaprolactone), poly ortho esters, polydioxanone, polyanhydrides, polyhydroxyalkanoate, and co-polymers of the above-mentioned materials. Other preferred materials for the scaffolds are block copolymers of PLA and Glycolic Acid (GA). Most preferred are copolymers of Poly Ethylene Glycol (PEG) and PLGA with a low PEG-content (~6% w/w).

Other synthetic polymers could be used as well. These include: Homo- or copolymers of: Glycolide, L-lactide, DL-lactide, meso-lactide, $\epsilon$-caprolactone, 1,4-dioxane-2-one, $\delta$-valerolactone, $\beta$-butyrolactone, $\gamma$-butyrolactone, $\epsilon$-decalactone, 1,4-dioxepane-2-one, 1,5,8,12-tetraoxacyclotetradecane-7-14-dione, 1,5-dioxepane-2-one, 6,6-dimethyl-1,4-dioxane-2-one, trimethylene carbonate. Block-copolymers of mono- or difunctional polyethylene glycol and polymers of Homo- or copolymers of: Glycolide, L-lactide, DL-lactide, meso-lactide, $\epsilon$-caprolactone, 1,4-dioxane-2-one, $\delta$-valerolactone, $\beta$-butyrolactone, $\gamma$-butyrolactone, $\epsilon$-decalactone, 1,4-dioxepane-2-one, 1,5,8,12-tetraoxacyclotetradecane-7-14-dione, 1,5-dioxepane-2-one, 6,6-dimethyl-1,4-dioxane-2-one, trimethylene carbonate. Block copolymers of mono- or difunctional polyalkylene glycol and polymers of Homo- or copolymers of: Glycolide, L-lactide, DL-lactide, meso-lactide, $\epsilon$-caprolactone, 1,4-dioxane-2-one, $\delta$-valerolactone, $\beta$-butyrolactone, $\gamma$-butyrolactone, $\epsilon$-decalactone, 1,4-dioxepane-2-one, 1,5,8,12-tetraoxacyclotetradecane-7-14-dione, 1,5-dioxepane-2-one, 6,6-dimethyl-1,4-dioxane-2-one, trimethylene carbonate. Blends of the above mentioned polymers. Blends of the above mentioned polymers and PEG.

A commonly used synthetic material is PLA—polylactic acid. This is a polyester, which degrades within the human body to form lactic acid, a naturally occurring chemical that is easily removed from the body. Similar materials are polyglycolic acid (PGA) and polycaprolactone (PCL): their degradation mechanism is similar to that of PLA, but they exhibit respectively a faster and a slower rate of degradation compared to PLA.

An MPEG-PLGA polymer can be synthesized as follows: MPEG, DL-lactide, glycolide and 4% (w/v) stannous octanoate in toluene are added to a vial in a glove box with nitrogen atmosphere. The vial is closed, heated and shaken until the contents are clear and homogeneous and then placed in an oven at 120-200° C. for 1 min-24 h. The synthesis can also be made in a solution in a suitable solvent (e.g. dioxane) to facilitate the subsequent purification. Then MPEG, DL-lactide, glycolide, 4% Stannous 2-ethylhexanoate and dioxane are added to a vial in a glove box with nitrogen atmosphere, and treated as above.

The polymer can be purified as follows: The polymer is dissolved in a suitable solvent (e.g. dioxane, tetrahydrofuran, chloroform, acetone), and precipitated with stirring in a non-solvent (e.g. water, methanol, ethanol, 1-propanol or 2-propanol) at a temperature of −40° C.-40° C. The polymer is left to settle, solvent discarded and the polymer is dried in a vacuum oven at 40° C.-120° C./overnight.

As illustrated in the foregoing, the base material of the scaffold can be made of material of synthetic and/or natural origin—including combinations thereof. Hence the scaffold can comprise combinations of proteins, polysaccharides and synthetic polymers.

In the present context, a temporary scaffold means a scaffold that disappears; is hydrolysed, is broken down, is biodegraded/bioresorbable/bioabsorbable/bioerodable, is dissolved or in other ways vanish from the wound site. This is a huge clinical advantage as there is no scaffold to remove from the cartilage (which is hard to access). Thus, the newly formed tissue is not disturbed or stressed by removal of the scaffold, or by leaving foreign material in the tissue. It is typically preferred that the scaffold is broken down during 1 day to 10 weeks—depending on the application. In one aspect of the invention, the scaffold is biodegradable.

The scaffold according to the invention is intended to promote cell in-growth. Apart from the chemical contents of the scaffold the physical structure of the scaffold can promote cell in-growth. One such physical characteristics is open pores, such as a porosity that allows cell migration.

Porosity is defined as $P=1-\rho(V/M)$
where P is the scaffold porosity, $\rho$ the density of the polymeric system used, M the weight, and V the volume of the fabricated scaffolds.

One embodiment of the invention relates to a porous scaffold. It is preferred that the porous scaffold has open interconnected pores.

The temporary scaffold may be either in a lyophilised form, in a fibrous form (woven or non-woven), in a foamed form or as a film. In all forms the binder of FGF-2 is accessible to the cells on both the outer and inner surface of porous/fibrous structure.

As illustrated in the examples the availability of the FGF-2 binder is essential to promote cell growth and their formation of new cartilage. If the FGF-2 binder is soluble (that is dissolvable) in the solvent used for formation of the scaffold, the FGF-2 binder will be dissolved. Typically, the FGF-2 binder is not soluble in the solvent used for formation of the scaffold. In those instances, it is preferred that the accessible binder is in the form as a particulate dispersion, or the accessible binder is in the form as a molecular dispersion. Whether the binder of FGF-2 is accessible can be tested as illustrated in example 7, where the release of GAG from a scaffold is quantified. An accessible binder has a release of more than 110%, such as more than 120%, or even more than 130%, 140% or more than 145%.

Since DS is not an abundant GAG in the ECM of cartilage, it is surprising that we see a chondrogenic effect and formation of cartilage. We speculate the chondrogenic effect of DS arises from its ability to bind FGF-2 (Penc S F et al. Dermatan sulfate released after injury is a potent stimulator of fibroblast growth factor-2 function. *J. Biol. Chem.* 273, 28116-28121 (1998)) as FGF-2 is a known stimulator of cartilage matrix synthesis.

Dermatan sulfate is abundant in the wound environment where it binds and activates growth factors such as fibroblast growth factor-2 (FGF-2) and FGF-7 (Trowbridge J M, Gallo R L. Dermatan sulfate: new functions from an old glycosaminoglycan. Glycobiology. 2002 September; 12(9):117R-25R). The minimum size of active dermatan sulfate is an octasaccharide for the activation of FGF-2, a decasaccharide for the activation of FGF-7 and active fractions found to be rich in monosulfated disaccharides and iduronic acid (Taylor, Rudisill and Gallo. Structural and sequence motifs in dermatan sulfate for promoting fibroblast growth factor-2 (FGF-2) and FGF-7 activity J Biol. Chem. 2005 Feb. 18; 280(7):5300-6, 2004). Higher sulfated dermatan sulfate preparations decreased or abolished cell proliferation indicating a preference for specific dermatan sulfate oligosaccharides capable of promoting FGF-2- and FGF-7-dependent cell proliferation.

In addition to the direct effect of dermatan sulfate on bFGF, dermatan sulfate is able to increase the levels of insulin growth factor 1 (IGF-1) within the cartilage matrix through a indirect mechanism. As the availability of IGF-1 is highly dependent on the binding to IGF-binding proteins (IGFBPs), the known binding sites for GAGs on IGFBPs is responsible for this effect. Six IGFBPs, designated IGFBP-1 to IGFBP-6, are known today and GAG binding sites has been found on all, except for IGFBP-4 (Hodgkinson S C, Napier J R, Spencer G S, Bass J J. Glycosaminoglycan binding characteristics of the insulin-like growth factor-binding proteins. J Mol. Endocrinol. 1994; 13:105-12). In cartilage IGFBP-2 and -3 and -6 are detected (Chevalier X, Tyler J A. Production of binding proteins and role of the insulin-like growth factor I binding protein 3 in human cartilage explants. Br J Rheumatol 1996; 35:515-22). That the interaction between dermatan sulfate and IGFBPs results in an increase in the level of free IGF-1 has been demonstrated in various studies (Moller A V, Jorgensen S P, Chen J W, Larnkjaer A, Ledet T, Flyvbjerg A, Frystyk. Glycosaminoglycans increase levels of free bioactive IGF-1 in vitro. Eur J Endocrinol 2006; 155:297-305, Arai T, Parker A, Busby W Jr, Clemmons D R. Heparin, heparan sulfate, and dermatan sulfate regulate formation of the insulin-like growth factor-I and insulin-like growth. J Biol Chem 1994; 269:20388-93). In this way more IGF-1 is able to bind to the IGF-receptors found on human chondrocytes and exert its anabolic effect as described below.

In a preferred aspect of the invention the binder of FGF-2 is Dermatan sulfate (DS). Heparan sulfate is another example of a FGF-2 binder important for cartilage development. Perlecan, a heparan sulfate proteoglycan (HSPG) in the developing growth plate, contains both HS and chondroitin sulfate (CS) chains. In a study by Smith et al. (Smith S M, West L A, Govindraj P, Zhang X, Omitz D M, Hassell. Heparan and chondroitin sulfate on growth plate perlecan mediate binding and delivery of FGF-2 to FGF receptors. JR Matrix Biol. 2006 nov.) FGF-2 was shown to bind to the HS chains of the Perlecan and additionally, only deliver of the FGF-2 to the FGF receptors when the CS chains were removed.

The molecular weight of the DS used can be in the range of 1-60 kDa, and it can be used either alone or in combination with other GAGs.

Another aspect of the invention relates to a temporary scaffold as described herein, comprising Hyaluronic acid (HA). That is, using HA instead of DS. As illustrated in the examples HA has a similar effect to DS—except that HA should be used at concentrations of 2-10%. In preferred embodiment hereof, the Mw of HA is between 500 and 2.000 kDA, such as in the range of 700-1.500 kDa. In particular embodiments the concentration of HA with a high Mw (1.500 kDa) is 2-5%. In another embodiment the concentration of HA with a low Mw (700 kDa) is 8-10%.

One aspect of the invention relates to the use of a temporary scaffold comprising an accessible binder of FGF-2 for the manufacture of a scaffold for the repair of tissue. Preferably for repair of damaged cartilage. In particular such use for repair of damaged articular cartilage.

A similar embodiment of the invention relates to a method of repairing damaged cartilage comprising the step of adding a temporary scaffold comprising an accessible binder of FGF-2 to the damaged site.

A related embodiment of the invention relates to a method of repairing damaged cartilage comprising the steps of both creating micro fractures in the bone surrounding the damaged cartilage; and adding a temporary scaffold comprising an accessible binder of FGF-2 to the damaged site. As illustrated in example 12, the present scaffolds have an increased absorption rate of cellular suspensions. Thus, the recruitment of mesenchymal stem cells from the bone marrow to the damaged site will be eased, whereby the effect of DS to direct growth and development of new cartilage will be enhanced.

One aspect of the invention relates to a method of producing a temporary scaffold comprising an accessible binder of FGF-2 comprising the steps of
(a) providing a solution of a scaffold material;
(b) adding a solution of the binder of FGF-2 to the solution of step (a) while mixing;
(c) pouring the mixed solution of step (b) into a mould;
(d) freeze-drying the mould of step (c).

EXAMPLES

Materials

Hyaluronan 1 (HA1) Mw>1.5 mDa
Hyaluronan 2 (HA2) Mw=700 kDa
MPEG-PLGA Scaffold Formation Purification of reagents: Ethyl acetate is distilled from calcium hydride under nitrogen. Dioxane is distilled from sodium/benzophenone under nitrogen. Toluene is distilled from sodium/benzophenone under nitrogen. DL-lactide and glycolide are recrystallized in dry ethylacetate in a nitrogen atmosphere and dried with vacuum. PEG/MPEG is dissolved in a suitable solvent (e.g. chloroform), precipitated in cold hexane, filtered, and dried overnight. Stannous 2-ethylhexanoate is vacuum-distilled and stored under nitrogen.

Synthesis of 2-30: 0.5 g MPEG2000, 4.15 g DL-lactide, 3.35 g glycolide and 4% (w/v) stannous octanoate in toluene are added to a vial in a glove box with nitrogen atmosphere. The vial is closed, heated and shaken until the contents are clear and homogeneous and then placed in an oven at 120-200° C. for 1 min to 48 hours, e.g. up to 6 h.

The synthesis can also be made in a solution in a suitable solvent (e.g. dioxane) to facilitate the subsequent purification. Then 0.5 g MPEG2000, 4.15 g DL-lactide, 3.35 g glycolide and 101 µL 4% (w/v) stannous octanoate and 8 g dioxane are added to a vial in a glove box with nitrogen atmosphere, and treated as above.

Purification of polymer: The polymer is dissolved in a suitable solvent (e.g. dioxane, tetrahydrofuran, chloroform, acetone), and precipitated with stirring in a non-solvent (e.g. water, methanol, ethanol, 1-propanol or 2-propanol) at a temperature of −40 to 40° C. The polymer is left to settle, solvent discarded and the polymer is dried in a vacuum oven at 40-120° C./overnight.

The polymers are analyzed with NMR-spectroscopy and GPC to confirm structure, molecular weight and purity.

Example 1

Hyaluronan (HA) in MPEG-PLGA Scaffolds

4% (w/v) MPEG-PLGA (2-30): 10.0 g is dissolved to 250 ml dioxane.

An aluminum mold (7.3×7.3×0.5 cm) is cooled to −5° C. 2 ml dioxane is added. This freezes to a thin film in the bottom to facilitate subsequent removal of the freeze-dried sheet.

Hyaluronan is placed in the bottom of a 50 ml beaker. 10 ml solution of 4% MPEG-PLGA is added and the mix is stirred with a homogenizer (15000 rpm). The mix is poured to the mold (still at −5° C.) on top of the frozen film of dioxane, and after the mix is frozen the mold is transferred to a freeze drier and dried (−20° C./1 h, +20° C./1 h). The scaffold is now a soft porous sheet with a high porosity. It is removed from the mold and stored overnight in a vacuum desiccator to remove traces of dioxane before biological testing. Series of scaffolds are made with 1) HA1, 2) HA2

| mg HA | HA (% w/w of solid) |
|-------|---------------------|
| 0     | 0                   |
| 4     | 1                   |
| 6     | 1.5                 |
| 8     | 2.0                 |
| 20    | 4.8                 |
| 40    | 9.1                 |

Example 2

Chondroitin Sulfate in Mpeg-PLGA Scaffolds 500 mg CS is dissolved to 5.00 ml.

10 ml solution (example 1) is added to a 25 ml beaker. CS-solution is added with stirring (homogenizer, 15000 rpm). This gives CS as finely dispersed solids in the polymer solution. The scaffold is then prepared as in example 1.

| ml CS 10% | CS (% w/w of solid) |
|-----------|---------------------|
| 80 µL     | 2.0                 |
| 160 µL    | 3.8                 |

Example 3

Dermatan Sulfate in MPEG-PLGA Scaffolds 500 mg DS is dissolved to 5.00 ml.

10 ml solution (example 1) is added to a 25 ml beaker. CS-solution is added with stirring (homogenizer, 15000 rpm). The scaffold is then prepared as in example 1.

| ml DS 10% | DS (% w/w of solid) |
|-----------|---------------------|
| 80 µL     | 2.0                 |
| 160 µL    | 3.8                 |

Example 4

Gelatin Scaffolds

1% HA: 0.2 g HA1 is dissolved in water to 20 mL
3% Gelatin: 6 g Gelatine is dissolved in water to 200 mL
All scaffolds are made by freeze-drying solutions with 2% (w/w) solids:

1% HA, 3% gelatine and water is mixed with stirring and 10 ml is frozen in an aluminium mold (7.3×7.3 cm2). These are then freeze-dried.

The freeze dried scaffolds are immersed in 0.1% EDC in acetone:water 90:10 for 2 hours. The scaffolds are then rinsed in water 34 times, frozen and freeze-dried again

| # | Water (mL) | HA 1% (mL) | Gelatine 3% (mL) | conc. of HA (% w/w of solids) |
|---|------------|------------|------------------|-------------------------------|
| 1 | 16         | 1          | 33               | 1                             |
| 2 | 15.3       | 2          | 32.7             | 2                             |
| 3 | 10         | 10         | 30               | 10                            |

Example 5

GAG in 1.5% MPEG-PLGA scaffolds 1.5% MPEG-PLGA (2-30): 3 g is dissolved to 200 ml with dioxane.

An aluminum mold (7.3×7.3×0.5 cm) is cooled to −5° C. 2 ml dioxane is added. This freezes to a thin film in the bottom to facilitate subsequent removal of the freeze-dried sheet.

GAG is placed in the bottom of a 50 ml beaker. 10 ml solution of 1.5% 2-30 is added and the mix is stirred with a homogenizer (15000 rpm). The mix is poured to the mold (still at −5° C.) on top of the frozen film of dioxane, and after the mix is frozen the mold is transferred to a freeze drier and dried −20° C. for 5 h and 20° C. for approx 15 h. It is removed from the mold and stored overnight in a vacuum desiccator to remove traces of dioxane before biological testing.

| mg DS | DS (% w/w of solid) |
|---|---|
| 0 | 0 |
| 0.75 | 0.5 |
| 1.5 | 1 |
| 3.1 | 2 |
| 7.9 | 5 |
| 6.25 | 4 |
| 13 | 8 |

| mg CS | CS (% w/w of solid) |
|---|---|
| 0.75 | 0.5 |
| 7.9 | 5 |

| mg heparin | heparin (% w/w of solid) |
|---|---|
| 0.75 | 0.5 |
| 7.9 | 5 |

Example 6

Cell Morphology and 3D Growth in Composite Scaffolds of MPEG-PLGA and Dermatan Sulfate Holding 4 Different Concentrations Scaffolds from example 5 are used.

In the dimethylmethylene blue (DMMB) assay the sulfated GAG content is measured by an increasing in OD 525 nm. The DMMB color solution was prepared according to Farndale et al. Briefly, 16 mg 1,9 dimethylmethylene blue was dissolved in 1 L of water containing 3.04 g glycine, 2.37 g NaCl and 95 ml 0.1 M HCl, pH 3.0. In order to measure the release of GAG from the MPEG-PLGA scaffolds containing 0, 1, 2 and 8% DS biopsies were punched out of each type of the scaffolds. These biopsies in duplicates were placed in a 48 well plate and 200 μl of DMMB solution were poured over the scaffolds corresponding to the amount necessary to cover the scaffolds. Five minutes later 100 μl of the color solution from the wells were transferred to a 96 well plate and measured at 525 nm. A Synergy™ HT Multi-Detection Microplate Reader from Bio-Tek was used.

The cell morphology and 3D growth in the MPEG-PLGA scaffold without DS showed in the first days of the study adherent cells growing as a combination of rounded cells and spindle-shaped cells. The cells were growing on the surface of the scaffolds. During the rest of the study all cells became spindle-shaped and from day 3 observed growing into the scaffolds. Adding 1% DS into the scaffolds did not change the way the cells were growing in this study compared to MPEG-PLGA scaffold without DS. Increasing the concentration of GAG to 2% resulted in day 1 in cells growing more in small region where the cells were growing close together. Increasing the concentration of DS to 4 and 8% increased the sizes of the regions and made it difficult to distinguish separate cells.

At day 3 the cells were beginning to spread more on the surface of the scaffolds. This effect were more pronounced in 2 and 4% compared to the scaffolds containing 8% DS.

Cells were at day 7 growing more on the surface of the scaffolds in the pure MPEG-PLGA scaffold and low concentration of DS compared to more in-growth into the scaffolds containing higher concentrations of DS and as a consequence of this cells were growing more spread with increasing concentrations of DS.

Example 7

GAG Release from Composite Scaffolds of MPEG-PLGA and Dermatan Sulfate

Scaffolds from example 5 are used.

In the dimethylmethylen blue (DMMB) assay the sulfated GAG content is measured by an increasing in OD 525 nm. The DMMB color solution was prepared according to Farndale et al. Briefly, 16 mg 1.9 dimethylmethylene blue was dissolved in 1 L of water containing 3.04 g glycine, 2.37 g NaCl and 95 ml 0.1 M HCl, pH 3.0. In order to measure the release of GAG from the MPEG-PLGA scaffolds containing 0, 1, 2 and 8% DS biopsies were punched out of each type of the scaffolds. These biopsies in duplicates were placed in a 48 well plate and 200 μl of DMMB solution were poured over the scaffolds corresponding to the amount necessary to cover the scaffolds. Five minutes later 100 μl of the color solution from the wells were transferred to a 96 well plate and measured at 525 nm. A Synergy™ HT Multi-Detection Microplate Reader from Bio-Tek was used.

Figure 4:
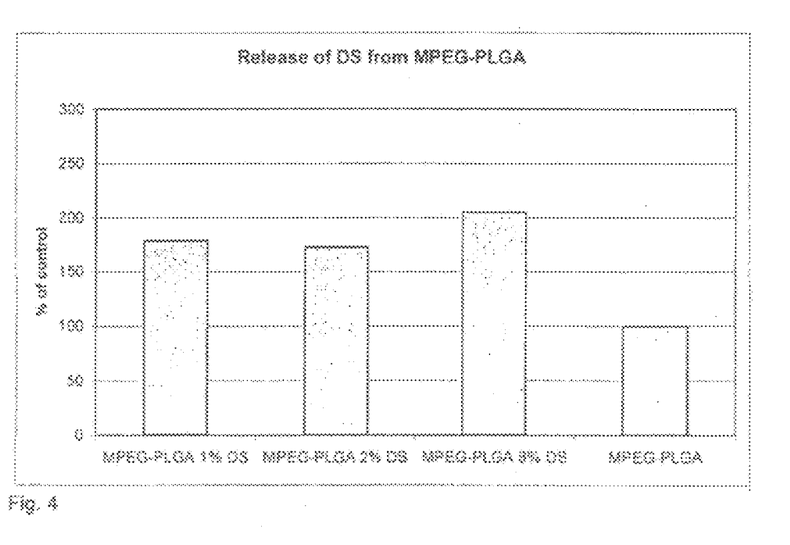
FIG. 4: release of GAG

The result of the study showed an immediate release of GAG from all the scaffolds containing DS and no release from the pure MPEG-PLGA scaffold (FIG. 4). A slightly higher release was observed in the 8% scaffold compared to the 1% and 2%.

This experiment demonstrates that the GAG present in the MPEG-PLGA scaffolds in the form of DS is non bound and accessible.

Example 8

Preparation, Cell Morphology and 3D Growth in Composite Scaffolds of MPEG-PLGA and Different Types of Gags Scaffolds from example 5 are used.

Evaluation was preformed by seeding primary human fibroblasts (passage 3) on the surface of the scaffolds in a density of $2.5 \times 10^4$ cells/cm$^2$ in a small volume of growth medium (10% FCS in DMEM) containing antibiotics (penicillin, streptomycin and Amphotericin B). The scaffolds were incubated at 37° C. at 5% $CO_2$ before additional growth medium was added. Evaluation of the cells attachment, morphology, growth and population of the scaffold were preformed on day 1, 3 and 7 by staining the cells with neutral red followed by evaluation using an Leica DMIRE2 inverted microscope fitted with a Evolution MP cooled color camera (Media Cybernetics). Digital images were taken using Image Pro Plus 5.1 software (Media Cybernetics).

The scaffolds containing the high concentration of GAGs showed in the first days of the study cells with a rounded morphology while the samples containing lower concentrations showed more spindle-shaped cells. All samples showed at day 3 and 7 cells growing with normal spindle-shaped morphology. No difference was observed in the morphology of the fibroblasts growing on scaffolds containing different sizes or types of GAGs.

Example 9

In Vitro 3D Generation of Cartilage

Scaffolds from examples 14 are used.

In this in vitro example the effect of different scaffold compositions on the 3-dimensional (3D) growth and matrix synthesis of human articular chondrocytes (hACs) was studied. The scaffold material was either MPEG-PLGA or gelatin, wherein a variety of different glycosaminoglycans (GAGs), including dermatan sulfate was added (Table 1).

Example 10 hACs were loaded ($1\times10^6$ hACs/cm$^2$) onto the different scaffolds together with a hydrogel [50 mg/mL fibrinogen (Sigma) and thrombin (Sigma)] and the cellular scaffolds were placed in individual culture wells (12 well plates, Nunc). Only passage 1 cells were used for the experiments. An optimized cell culture medium [DMEM/F12 (GIBCO) containing 10% fetal bovine serum (Cambrex), gentamicin (59 µg/mL, GIBCO), fungizone (2.5 µg/mL, GIBCO) and ascorbic acid (Sigma)] was added and the 3D scaffold systems were cultured for 3 weeks.

The design consisted of 2× triplicates of each scaffold type.

At the of the culture period, scaffolds were removed from the culture wells and each scaffold was divided into two parts. One part were processed for histology, including immunohistochemistry (IHC) and the second part were processed for gene expression.

TABLE 1

| Scaffold ID | Composition |
|---|---|
| S1 | 1% HA1 |
| S2 | 1.5% HA1 |
| S3 | 2% HA1 |
| S4 | 4.8% HA1 |
| S5 | 9.1% HA1 |
| S6 | 2% CS |
| S7 | 3.8% CS |
| S8 | 1% HA2 |
| S9 | 2% HA2 |
| S10 | 4.8% HA2 |
| S11 | 9.1% HA2 |
| S12 | 2% DS |
| S13 | 3.8% DS |
| S14 | G/1% HA1 |
| S15 | G/2% HA1 |
| S16 | G/10% HA1 |
| S17 | G/ |
| S18 | Control |

HA: Hyaluronic acid, CS: Chondroitin sulfate, DS: dermatan sulfate.

Results

The following results were observed during the experiment as described below.

Histology/IHC

Based on H&E- and safranin O staining every scaffold type was scored, depending on cellular distribution, cellular morphology and degree of matrix synthesis (table 2).

TABLE 2

| Scaffold ID | Score |
|---|---|
| S1 | 1 |
| S2 | 1 |
| S3 | 2 |
| S4 | 1 |
| S5 | 2 |
| S6 | 1 |
| S7 | 2 |
| S8 | 1 |
| S9 | 1 |
| S10 | 2 |
| S11 | 3 |
| S12 | 3 |
| S13 | 3 |
| S14 | 1 |
| S15 | 1 |
| S16 | 1 |
| S17 | 1 |
| S18 | 2 |

Score: 1 = not good, 2 = ok, 3 = good.

Figure 1:
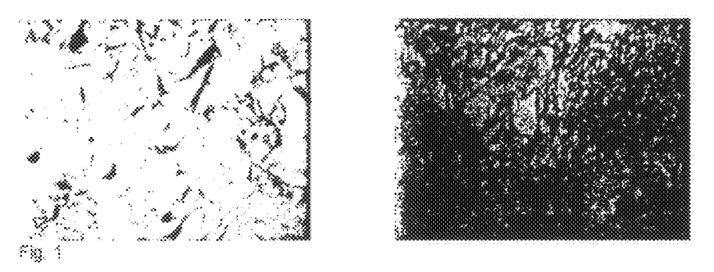

Scaffolds having a score of 1, contained generally a lot of cellular debris (FIG. 1A), and had a very uneven distribution of hACs. Some even seemed completely acellular. All scaffolds made of gelatin, showed very bad histology and were all totally acellular (1B).

Figure 2:
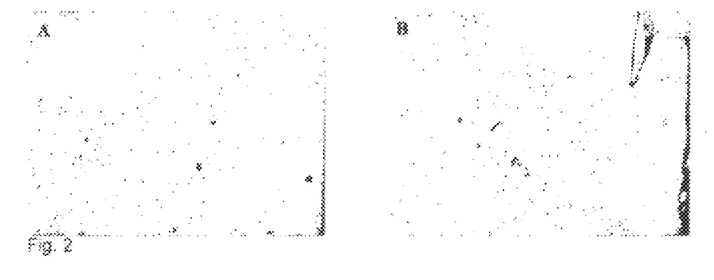

As listed in table 2, the two scaffold types containing dermatan sulfate, demonstrated a high degree of matrix synthesis and a good cellular distribution. No significant signs of cellular debris were observed and generally a nice morphology was observed. These observations are illustrated on FIG. 2, which is representative for this scaffold type.

Only one scaffold type containing HA (S11) had a good score.

Figure 3:
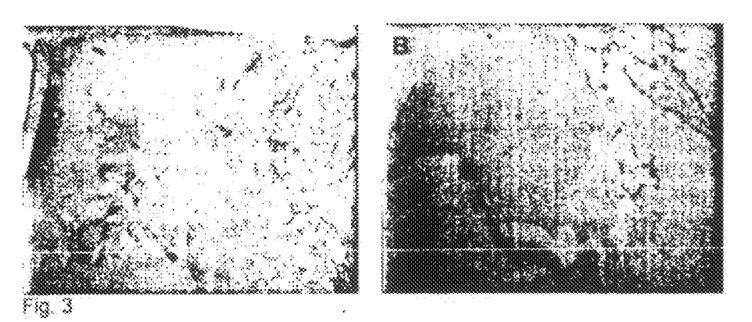

IHC analysis with monoclonal antibodies against aggrecan (FIG. 3A) and collagen type 2 (FIG. 3B), demonstrated the hACs loaded onto scaffolds containing dermatan sulfate synthesized these chondrogenic matrix molecules.

Gene Expression

The results from gene expression analysis are listed in table 3.

TABLE 3

| Gene expression results obtained by RT-PCR and subsequent UV-visualization. | | |
|---|---|---|
| Scaffold ID | Col2 | Sox9 |
| S1 | ++ | ++ |
| S2 | ++ | + |
| S3 | +++ | +++ |
| S4 | ++ | +++ |
| S5 | ++ | + |
| S6 | + | + |
| S7 | ++ | ++ |
| S8 | ++ | + |
| S9 | + | + |
| S10 | + | ++ |
| S11 | ++ | +++ |
| S12 | +++ | +++ |
| S13 | ++ | +++ |
| S14 | ++ | + |
| S15 | N/A | N/A |
| S16 | N/A | N/A |
| S17 | ++ | ++ |
| S18 | ++ | ++ |

+ = weak signal, +++ = strong signal.

Analyzing the different scaffold types by RT-PCR, with specific primers for Col2 and Sox9, demonstrated that the expression of the chondrogenic markers in S3, S11, S12 and S13, were upregulated. This indicates a chondrogenic effect, arising from the molecules contained within the scaffold types.

Looking at the histology data and the gene expression data together suggests that scaffold types composed of MPEG-PLGA containing dermatan sulfate have a clear chondrogenic effect on hACs loaded onto these scaffolds.

Example 11

Human articular chondrocytes (hACs), passage 1, were loaded ($0.5 \times 10^6/cm^2$) onto the different scaffolds in a volume of 80 μL optimized growth medium (GM) consisting of DMEM/F12 supplemented with fetal bovine serum (10%), gentamicin (59 μg/mL), fungizone (2.5 μg/mL) and ascorbic acid.

Scaffolds were placed for 1 hour at 37° C. and 5% $CO_2$ in order to allow adherence of hACs to the scaffold structure. Subsequently GM was added.

GM was changed four times per week.

In Table 4 the tested scaffolds are listed.

TABLE 4

| Scaffold ID | Composition |
| --- | --- |
| S1 | 1% DS |
| S2 | 2% DS |
| S3 | 5% DS |
| S4 | 10% DS |
| S5 | 1% HA |
| S6 | 2% HA |
| S7 | 5% HA |
| S8 | 10% HA |
| S9 | Control |

DS: dermatan sulfate; HA: hyaluronic acid, HA1

The expressions of chondrogenic marker genes were analyzed after 1 day. mRNA were purified from each scaffold and cDNA synthesis (reverse transcription [RT]) was done immediately.

PCR reactions were done using specific primers for collagen type II and Sox9, two well-know chondrocytic marker genes.

Results are summarized in Table 5.

TABLE 5

Gene expression results obtained by RT-PCR after 1 day.
Day 1

| Scaffold ID | Col2 | Sox9 |
| --- | --- | --- |
| S1 | ++ | ++ |
| S2 | ++ | ++ |
| S3 | ++ | +++ |
| S4 | +++ | +++ |
| S5 | +++ | +++ |
| S6 | ++ | ++ |
| S7 | ++ | + |
| S8 | + | + |
| S9 | + | + |

+ = week signal, +++ = strong signal.

The RT-PCR analysis demonstrated that increasing concentrations of DS in the scaffold structure resulted in an increased expression of both collagen type II and Sox9.

The opposite expression pattern was observed for scaffolds containing HA. HA in low concentrations resulted in higher expression compared to HA in high concentrations.

Example 12

In order to evaluate the effect of DS and HA within the MPEG-PLGA scaffold on the absorption ability, 80 μL cell suspension ($0.5 \times 10^6$ human articular chondrocytes) was loaded on the different scaffold compositions listed in Table 6.

The absorption ability was recorded at room temperature.

TABLE 6

Absorption ability

| Scaffold ID | Composition | Absorption ability (min) |
| --- | --- | --- |
| S1 | 1% DS | 20 |
| S2 | 2% DS | 20 |
| S3 | 5% DS | 15 |
| S4 | 10% DS | 15 |
| S5 | 1% HA | 30 |
| S6 | 2% HA | 30 |
| S7 | 5% HA | 30 |
| S8 | 10% HA | 35 |
| S9 | Control | 40 |

The example demonstrates that MPEG-PLGA containing 10% or 5% DS has the highest absorption ability, while the control MPEG-PLGA has the lowest.

FIGURES

FIG. 1: (A) S2, H&E staining, (B) S14 H&E staining.
FIG. 2: (A) S12, H&E staining. (B) S13, H&E staining.
FIG. 3: (A) S13, aggrecan, (B) Col2

The invention claimed is:

1. A temporary scaffold comprising a scaffold material and dermatan sulfate (DS) particles dispersed throughout the scaffold material and the surface of the scaffold material, wherein the dispersed DS particles are not bonded to the scaffold material, wherein the concentration of dispersed unbound DS particles present throughout the scaffold material is from 1 to 10 weight percent, and wherein the dispersed unbound DS particles are released from the scaffold material by more than 110% as measured by a dimethyl methylene blue assay and wherein the unbound DS particles provide a chondrogenic effect.

2. The scaffold according to claim 1, wherein the scaffold material is synthetic.

3. The scaffold according to claim 1, wherein the scaffold material is biodegradable.

4. The scaffold according to claim 1, wherein the scaffold has open interconnected pores.

5. The scaffold according to claim 4, wherein the scaffold material is synthetic.

6. The scaffold according to claim 1 wherein the scaffold material is selected from the group consisting of PLA (polylactide), PGA (polyglycolide), PLGA (poly(lactide-co-glycolide)), MPEG-PLGA, PCL (polycaprolactone), poly ortho esters, polydioxanone, polyanhydrides, polyhydroxyalkanoate, and co-polymers thereof.

7. The scaffold according to claim 3, wherein the scaffold material is synthetic.

8. The scaffold according to claim 1, wherein the unbound DS particles provide an accessible binder of fibroblast growth factor-2.

9. A method to repair damaged cartilage, comprising the step: adding the scaffold according to claim 1 to damaged cartilage.

10. A method to repair damaged articular cartilage, comprising the step: adding the scaffold according to claim 1 to damaged articular cartilage.

11. A method of producing a temporary scaffold according to claim 1 comprising the steps of
   (a) providing a solution of a scaffold material;
   (b) adding a solution of dermatan sulfate to the solution of step (a) while mixing;
   (c) pouring the mixed solution of step (b) into a mould; and
   (d) freeze-drying the mixed solution following step (c), wherein dermatan sulfate particles are dispersed throughout the scaffold material and scaffold surface and is not bonded to the scaffold material.

* * * * *